United States Patent [19]

Iwamoto

[11] Patent Number: 5,034,113
[45] Date of Patent: Jul. 23, 1991

[54] REFERENCE ELECTRODE ASSEMBLY OF A SILVER/SILVER CHLORIDE CONSTRUCTION

[75] Inventor: Yasukazu Iwamoto, Miyanohigashi, Japan

[73] Assignee: Horiba, Ltd., Kyoto, Japan

[21] Appl. No.: 417,882

[22] Filed: Oct. 6, 1989

[30] Foreign Application Priority Data

Oct. 17, 1988 [JP] Japan .................. 63-262222

[51] Int. Cl.$^5$ ............................. G01N 27/30
[52] U.S. Cl. .................................. 204/435
[58] Field of Search ............... 204/416–419, 204/435

[56] References Cited

U.S. PATENT DOCUMENTS

| | | | |
|---|---|---|---|
| 3,227,643 | 1/1966 | Okun et al. | 204/415 |
| 3,455,793 | 7/1969 | Watanabe et al. | 204/435 |
| 3,785,948 | 1/1974 | Hitchman et al. | 204/415 |
| 3,835,010 | 9/1974 | Levins | 204/435 |

Primary Examiner—T. Tung
Attorney, Agent, or Firm—Joseph W. Price

[57] ABSTRACT

An improved reference electrode assembly is provided to solve blockage problems that can occur upon contamination of the internal solution in a housing member. An absorbent means can be provided for removing silver ions through the reaction of an alkali metal ion with a tetraphenylborate ion to produce a compound larger than that of a silver ion and a tetraphenylborate ion. The absorbent material can, for example, be a porous activated carbon or a silica gel, and can be positioned between the internal electrode of the reference electrode assembly and the liquid junction.

12 Claims, 1 Drawing Sheet

REFERENCE ELECTRODE ASSEMBLY OF A SILVER/SILVER CHLORIDE CONSTRUCTION

BACKGROUND OF THE INVENTION

1. Field of the Invention

The present invention relates to an improvement in a reference electrode of a silver/silver chloride electrode composition for immersion in an internal solution to serve as an internal electrode and, more particularly, to an electrode assembly capable of minimizing any blockage of a liquid junction.

2. Description of Related Art

In a reference electrode having the above-described construction, a soluble silver ion ($Ag^+$) is dissolved from the silver/silver chloride electrode during the use of the reference electrode, or dissolved chloro complex ions are formed by the following reactions (1) and (2) listed below as equations, and the ions are brought into contact with a lower potential chloride ionized water at a liquid junction to make the above-described respective reactions progress in the left direction, whereby AgCl (silver chloride) is settled out of the solution.

$$AgCl + Cl^- \rightleftharpoons AgCl_2^- \tag{1}$$

$$AgCl_2^- + Cl^- \rightleftharpoons AgCl_3^{2-} \tag{2}$$

In particular during the continuous use of such a reference electrode at a high temperature of 60° C. or more, the concentration of silver ion and chloro complex ion can be increased and the silver ion will be turned into silver chloride during a reduction of temperature, to eventually cause a blockage of the liquid junction. Such a reference electrode, during continuous use at 100° C., will cause the liquid junction to be blocked with silver chloride within about several days. In addition, in the case where interferential substances, such as protein, silver, mercury, and $H_2S$, contained in a sample to be tested, enter the internal solution through the liquid junction, there is the further possibility that these interferential substances can change the electrical potential of the internal electrode, and the interferential substances may further act upon the silver ion to additionally form soluble precipitates which will also block the liquid junction.

Because of these problems, the internal solution must be periodically exchanged with a new solution to prevent the quantity of silver ions and chloro complex ions existing in the internal solution from increasing, or the internal solution must be compulsorily leaked to prevent the sample being tested from being sucked up due to any change in pressure resulting from a temperature cycle and the like.

However, exchanging the internal solution does not effectively remove silver ions, which are a dominant cause of the blockage of the liquid junction, and maintenance problems are also created in making such exchanges. In addition, the latter measure has shown disadvantages in that the reference electrode is complicated in construction, expensive, and becomes ineffective during continuous use.

SUMMARY OF THE INVENTION

The present invention has been achieved in view of the above-described problems in the prior art, and it is an object of the present invention to provide an improved reference electrode assembly capable of preventing a liquid junction from being blocked by effectively removing any silver ions and chloro complex ions which have been dissolved in an internal solution, and which can turn into a difficult soluble precipitate. The electrode assembly can also prevent an electrical potential of an internal electrode from changing due to any interferential substances by adsorbing the interferential substances entering therein through the liquid junction.

In order to achieve the above-described objects, a reference electrode assembly according to the present invention is characterized by an adsorbent material comprising a compound of an alkali metal ion and a tetraphenylborate ion or a nitrogen-containing organic substance (for example, a tertiary ammonium salt and the like) and a tetraphenylborate ion having a solubility product larger than that of a compound of a silver ion and a tetraphenylborate ion. These compounds are provided in a specific carrier material having an improved adsorptivity in an internal solution.

With the above-described construction, silver ions and chloro complex ions, dissolved from the internal electrode, are thereby taken into the adsorbent material to be bound with the tetraphenyl boric acid ion, thereby preventing silver chloride from being formed. In addition, since the carrier of the adsorbent is superior in physical adsorptivity, any interferential substances, such as protein, silver, mercury, and $H_2S$, are also adsorbed by the carrier, and any change of an electrode potential due to the interferential substances is prevented from occurring even though the interferential substances may enter the internal solution through the liquid junction.

The preferred embodiments of the present invention are below-described with reference to the drawings.

DESCRIPTION OF THE PREFERRED EMBODIMENTS

The following description is provided to enable any person skilled in the art to make and use the invention, and sets forth the best modes contemplated by the inventor of carrying out his invention. Various modifications, however, will remain readily apparent to those skilled in the art, since the generic principles of the present invention have been defined herein specifically to provide an improved and economical reference electrode that resolves recurring problems in the prior art.

Figure 1:
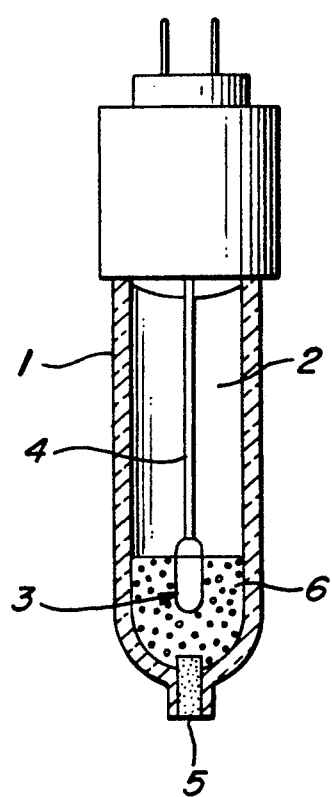
FIG. 1 is a sectional view showing a reference electrode according to one preferred embodiment of the present invention.

Referring to FIG. 1, which shows one preferred embodiment of a reference electrode according to the present invention, reference numeral 1 designates a cylindrical member formed as a tubular member, such as a glass tube, and reference numeral 2 designates an internal solution, for example, an aqueous solution of KCL, charged within the cylindrical member 1.

Reference numeral 3 designates an internal electrode, formed of a silver/silver chloride electrode obtained by adhering molten silver chloride to a pointed end of a silver rod 4 and immersed in the internal solution 2. Reference numeral 5 designates a liquid junction formed of, for example, known ceramic material and provided in a lower end portion of the cylindrical member 1, reference numeral 6 designates an adsorbent material provided in the internal solution 2 which is obtained by impregnating a filtration carrier formed of an activated carbon having a superior physical adsorptivity characteristic with K-TPB (tetraphenyl potassium borate) under an insolubilized condition. Activated carbon is porous and has a large surface area. Alternatively, silica gel can be used.

This adsorbent material 6 is produced, for example, as follows:

(1) 0.5 mol/liter Na-TPB (tetraphenyl sodium borate) of 50 ml is prepared.

(2) Activated carbon is washed with an ion-exchanged water until a pH of 6 to 8 is achieved.

(3) The activated carbon is dried (about 12 hours at 60° C.).

(4) Activated carbon of about 30 g, which has been dried, is added in 0.5 mol/liter Na-TPB of 50 ml, and the resulting mixture is stirred about 10 minutes by means of a stirrer.

(5) The activated carbon, which has been subjected to the above-described treatment (4), is then sufficiently dried.

(6) Activated carbon, which has been subjected to the above-described treatment (5), is added in 1 mol/liter KCl (potassium chloride) of 50 ml, and the resulting mixture is stirred about 20 minutes by means of a stirrer.

Applying this treatment, the reaction shown by the following Equation (3) is brought about whereby the Na-TPB, which has been physically adsorbed in activated carbon, is replaced by K-TPB and held in the activated carbon.

$$Na\text{-}TPB + KCl \rightarrow K\text{-}TPB + NaCl \tag{3}$$

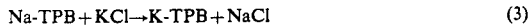

(7) After several cycles of decantation are repeated, activated carbon, which has been subjected to the above-described treatment (6), is washed with an ion-exchanged water which removes the sodium chloride and then dried (about 12 hours at 60° C.).

About one gram of adsorbent material 6, produced in the above-described manner, is added into, for example, an internal solution 2 of about 10 ml. The adsorbent material 6 comprises an insoluble K-TPB, which is a compound of potassium (k) ion having a solubility product larger than that of the silver ion and the tetraphenyl boric acid ion. The adsorbent material 6 is impregnated into activated carbon and is physically located in the internal solution 2 between the electrode and the liquid junction. Silver ions and chloro complex ions, which are dissolved from an internal electrode 3 formed of silver/silver chloride, are thereby taken into the adsorbent material 6 and combined with the tetraphenyl boric acid ions in the adsorbent material 6 to be turned into precipitates that are relatively difficult to dissolve, thereby preventing silver chloride from being formed. An example of a chemical reaction for this relatively insoluble participate is as follows:

$$K\text{-}TPB + AgCl \rightarrow Ag\text{-}TPB + KCl$$

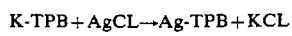

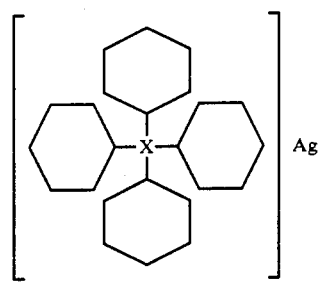

In addition, since the activated carbon, which can be the carrier of the adsorbent material 6, is superior in physical adsorptivity, the interferential substances, such as protein, silver, mercury, and $H_2S$, are adsorbed by the activated carbon before they reach the electrode, and any possible change on the electrode potential due to them can be prevented even though they may enter the internal solution 2 through the liquid junction 5.

Figure 2:
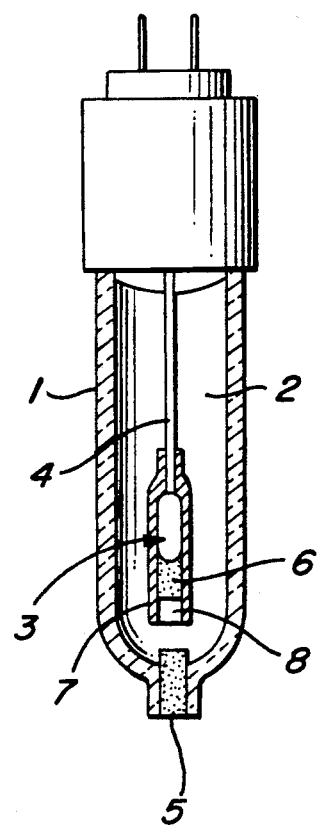
FIG. 2 is a sectional view showing a reference electrode according to another preferred embodiment of the present invention.

FIG. 2 shows the reference electrode assembly according to another preferred embodiment of the present invention. In this embodiment, an internal electrode 3 formed of silver/silver chloride is housed in an internal tube 7, such as a thermoshrinkable tube. The adsorbent material 6 can be placed within this internal tube 7. An inside liquid junction 8 formed of, for example, plastic fibers or a molecular sieve, can be formed at a lower end of the internal tube 7 to form a so-called double-junction-type reference electrode assembly.

In the case where the volume of the internal solution is 10 ml, the same effect as in the reference electrode assembly shown in the above-described FIG. 1 can be achieved by charging the internal tube 7 with a slight quantity of the adsorbent material 6 of about 0.05 g. The quantity of the adsorbent material 6 required over that of the first embodiment can be reduced to 1/20, so that the cost can be remarkably reduced.

The present invention is not limited by the above-described preferred embodiments, but can be variously modified. A carrier superior in physical adsorptivity can be used; for example, a molecular sieve may be used in addition to the above-described activated carbon and silica gel. In the case where the reference electrode is formed in the double-junction-type, as shown in FIG. 2, it is not always necessary to use activated carbon as the carrier. The inside liquid junction 8 formed of, for example, plastic fibers may be used as the carrier.

In addition, compounds of alkali metal ions having a solubility product larger than that of silver ion or nitrogen-containing organic substances, such as quaternary ammonium salt, and tetraphenyl boric acid ion, such as $NH_4$-TPB, may be used as substances to be carried in the carrier in addition to the above-described K-TPB. Solubility product, as used herein, means a product of the concentrations (mol/liter) of both an anion and a cation in the saturated solution.

According to the present invention, even though the reference electrode is continuously used (particularly at high temperatures), the blockage of the liquid junction with silver chloride can be prevented. In the conventional reference electrode, silver chloride, which has blocked the liquid junction, has further behaved like an ion electrode, thereby making the electrode potential fluctuate greatly depending upon the pH value of the sample liquid. However, according to the present invention, such a fluctuation of the electrode potential can be remarkably reduced. In addition, since the adsorbent material has not only a physical, but also a chemical adsorptive characteristic, not only silver ions and chloro complex ions, but also many kinds of interferential substances can be effectively adsorbed.

Finally, since the quantity of the internal solution that is expended with the lapse of time is reduced, the deterioration in performance of the electrode assembly, such as an increase of interliquid potential difference, with the lapse of time can be lessened.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. An improved reference electrode assembly, comprising:
   a housing member;
   a liquid junction formed in the housing member;
   an internal solution provided in the housing member;
   an internal electrode of a silver/silver salt composition immersed within the internal solution, and
   a solid absorbent means carrying a tetraphenylborate compound, provided adjacent the internal electrode and between the internal electrode and the liquid junction, for removing sliver ions, whereby blockage of the liquid junction is prevented.

2. The improved reference electrode assembly of claim 1 wherein said compound is tetraphenyl boric acid.

3. The improved reference electrode assembly of claim 1 wherein the absorbent means includes a filtration material.

4. The improved reference electrode assembly of claim 1 further including an inner housing surrounding the internal electrode and having a second liquid junction for providing communication between the internal solution and the internal electrode, the adsorbent means being positioned within the inner housing.

5. The improved reference electrode assembly of claim 4 wherein the absorbent means includes activated carbon.

6. The improved reference electrode assembly of claim 4 wherein the adsorbent means includes a carrier material that is porous.

7. In a reference electrode assembly of a silver/silver chloride composition, immersed in an internal solution as an internal electrode and having a liquid junction, the improvement comprising:
   a solid adsorbent carrier material carrying a tetraphenylborate compound, the carrier material being positioned between the liquid junction and the reference electrode, whereby any dissolved silver ions and chloro complex ions contacting the carrier material can be absorbed into the carrier material and combined with the tetraphenylborate compound to form a relatively insoluble precipitate.

8. A reference electrode assembly as set forth in claim 7 wherein the carrier material is a molecular sieve.

9. A reference electrode assembly as set forth in claim 7 wherein the carrier material is silica gel.

10. A reference electrode assembly as set forth in claim 7 wherein the carrier material is activated carbon.

11. A reference electrode assembly as set forth in claim 10 wherein said compound is a quaternary ammonium salt.

12. A reference electrode assembly as set forth in claim 10 wherein said compound is tetraphenyl boric acid.

* * * * *